(12) United States Patent
Tanaka et al.

(10) Patent No.: US 9,632,062 B2
(45) Date of Patent: Apr. 25, 2017

(54) ULTRASONIC PIPE MEASUREMENT APPARATUS

(71) Applicant: YOKOGAWA ELECTRIC CORPORATION, Musashino-shi, Tokyo (JP)

(72) Inventors: Yoshiaki Tanaka, Tokyo (JP); Kazunori Miyazawa, Tokyo (JP); Ken'ichi Kamada, Tokyo (JP); Satoshi Kato, Tokyo (JP); Yosuke Ishii, Tokyo (JP); Sho Fujita, Tokyo (JP); Yukiyo Akisada, Tokyo (JP); Nobuo Okabe, Tokyo (JP); Hiroaki Tanaka, Tokyo (JP); Minako Terao, Tokyo (JP)

(73) Assignee: Yokogawa Electric Corporation, Tokyo (JP)

(*) Notice: Subject to any disclaimer, the term of this patent is extended or adjusted under 35 U.S.C. 154(b) by 161 days.

(21) Appl. No.: 14/483,797

(22) Filed: Sep. 11, 2014

(65) Prior Publication Data

US 2015/0068311 A1    Mar. 12, 2015

(30) Foreign Application Priority Data

Sep. 12, 2013   (JP) .................................. 2013-189360

(51) Int. Cl.
*G01N 29/04* (2006.01)
*G01B 17/02* (2006.01)
*G01N 17/00* (2006.01)
*G01N 29/07* (2006.01)
*G01N 29/11* (2006.01)

(52) U.S. Cl.
CPC ............. *G01N 29/04* (2013.01); *G01B 17/02* (2013.01); *G01N 17/00* (2013.01); *G01N 29/043* (2013.01);

(Continued)

(58) Field of Classification Search
CPC ...... G01N 2291/105; G01N 2291/2634; G01N 29/07; G01N 29/11; G01N 29/043

(Continued)

(56) References Cited

U.S. PATENT DOCUMENTS 3,898,840 A    8/1975   McElroy
4,523,468 A *  6/1985   Derkacs ................. G01N 29/07
                                                           73/598

(Continued)

FOREIGN PATENT DOCUMENTS

EP    1637877 A1    3/2006
EP    2485026 A1    8/2012

(Continued)

OTHER PUBLICATIONS

Drinkwater B W et al: "Ultrasonic arrays for non-destructive evaluation: A review", NDT & E International, Butterworth-Heinemann, Oxford, GB, vol. 39, No. 7, Oct. 1, 2006 (Oct. 1, 2006), pp. 525-541, XP027969035, ISSN: 0963-8695 [Retrieved on Oct. 1, 2006].

*Primary Examiner* — Michael A Lyons
*Assistant Examiner* — Suman K Nath
(74) *Attorney, Agent, or Firm* — Sughrue Mion, PLLC (57) ABSTRACT

An ultrasonic pipe measurement apparatus includes: a plurality of ultrasonic transceivers discretely disposed on a pipe wall of a pipe; and a control unit configured to control the plurality of ultrasonic transceivers and detect a generation point of damage caused in the pipe based on an ultrasonic signal exchanged between the ultrasonic transceivers.

8 Claims, 9 Drawing Sheets

(52) U.S. Cl.
CPC ............ *G01N 29/07* (2013.01); *G01N 29/11* (2013.01); *G01N 2291/015* (2013.01); *G01N 2291/023* (2013.01); *G01N 2291/0289* (2013.01); *G01N 2291/02854* (2013.01); *G01N 2291/2634* (2013.01)

(58) Field of Classification Search
USPC .................... 73/622, 628, 632, 641, 592
See application file for complete search history.

(56) References Cited

U.S. PATENT DOCUMENTS

| | | | |
|---|---|---|---|
| 4,603,584 A | 8/1986 | Bartle et al. | |
| 6,148,672 A * | 11/2000 | Cawley | G01N 29/223 73/622 |
| 9,404,903 B2 * | 8/2016 | Batzinger | G01N 33/00 |
| 2004/0255678 A1 | 12/2004 | Nagashima et al. | |
| 2009/0084184 A1 * | 4/2009 | Dijkstra | G01N 29/225 73/623 |
| 2009/0217763 A1 * | 9/2009 | Yamano | G01N 29/043 73/622 |
| 2014/0190264 A1 * | 7/2014 | Barshinger | G01N 29/04 73/592 |

FOREIGN PATENT DOCUMENTS

| | | |
|---|---|---|
| GB | 1266342 A | 3/1972 |
| GB | 2462078 A | 1/2010 |
| JP | 59131161 A | 7/1984 |
| JP | 11023539 A | 1/1999 |
| JP | 2000-329751 A | 11/2000 |
| JP | 2005-10055 A | 1/2005 |
| WO | 2011071241 A2 | 6/2011 |

* cited by examiner

FIG. 3A
US1 DRIVING WAVEFORM

FIG. 3B
US1 RECEPTION WAVEFORM
REFLECTION WAVE R1

FIG. 3C
US2 RECEPTION WAVEFORM
REFLECTION WAVE R2

FIG. 3D
US3 RECEPTION WAVEFORM
REFLECTION WAVE R3

<RECEPTION WAVEFORM OF US1>

FIG. 6A
US1 DRIVING WAVEFORM

FIG. 6B
REFLECTION WAVE R1
NO DAMAGE

FIG. 6C
REFLECTION WAVE R1
DAMAGE EXISTS

<RECEPTION WAVEFORM OF US2>

FIG. 6D
US1 DRIVING WAVEFORM

FIG. 6E
TRANSMISSION WAVE P1
NO DAMAGE

FIG. 6F
TRANSMISSION WAVE P1
DAMAGE EXISTS

FIG. 8

FIG. 9

ULTRASONIC PIPE MEASUREMENT APPARATUS

CROSS-REFERENCE TO RELATED APPLICATION

This application claims priority from Japanese Patent Application No. 2013-189360 filed with the Japan Patent Office on Sep. 12, 2013, the entire content of which is hereby incorporated by reference.

BACKGROUND

1. Technical Field

The present disclosure relates to an ultrasonic pipe measurement apparatus.

2. Related Art

An ultrasonic pipe measurement apparatus is an apparatus employs an ultrasonic wave to measure a generation point and size or amount of such as the damage occurred by corrosion or erosion in the pipe and scale attached to the inside of the pipe (that is, the conditions of a pipe). As an apparatus for detecting and measuring corrosion and erosion in a pipe, an ultrasonic thickness meter has been known. The ultrasonic thickness meter measures the wall thickness of a pipe using the propagation time of ultrasonic waves to measure the thickness loss due to corrosion or erosion.

Figure 8:
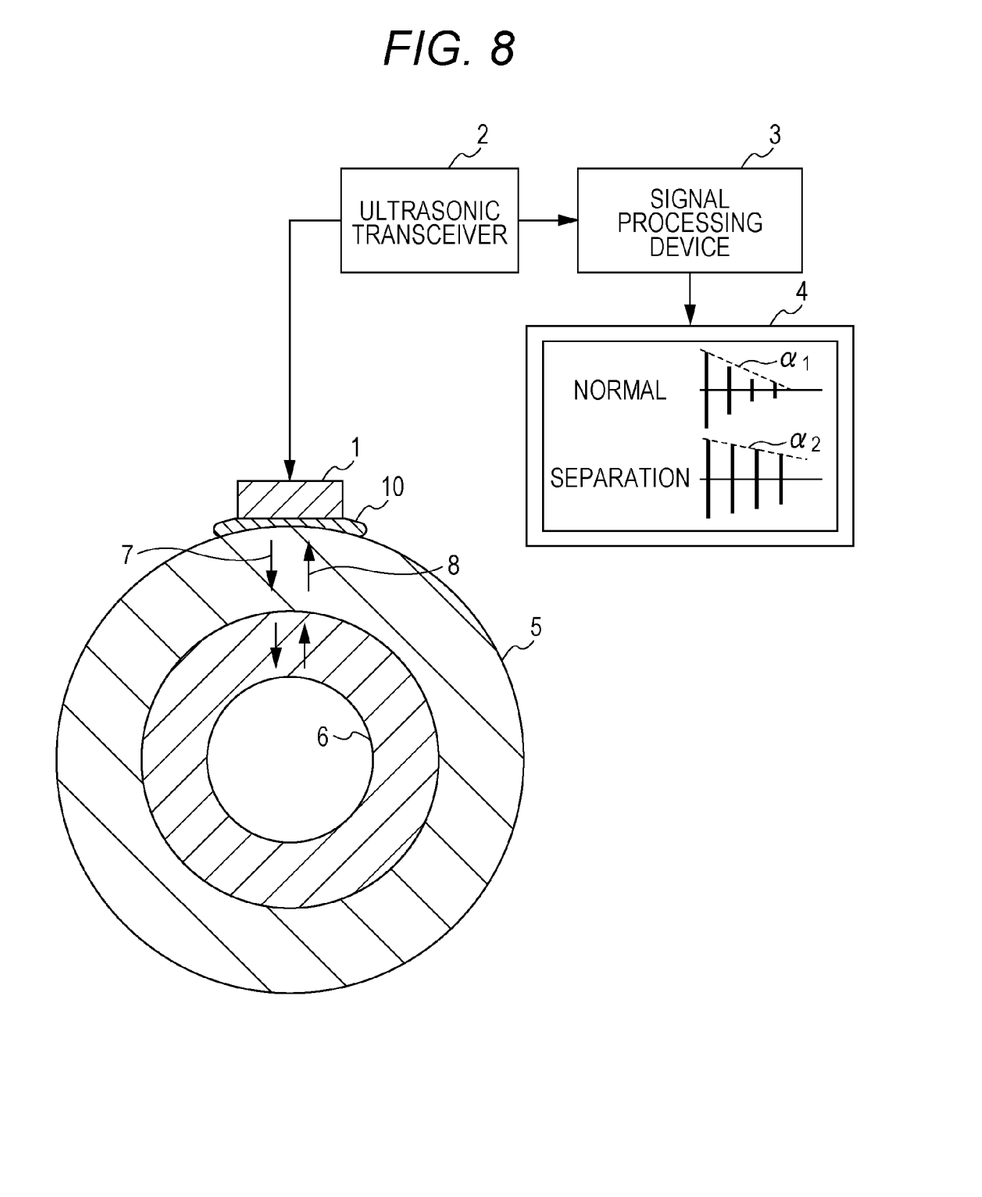
FIG. 8 is an explanatory diagram illustrating an example of an ultrasonic thickness meter.

FIG. 8 is a diagram illustrating an exemplary structure of the ultrasonic thickness meter (JP-A-2000-329751). As illustrated in FIG. 8, this ultrasonic thickness meter includes a piezoelectric ultrasonic transducer 1, an ultrasonic transceiver 2, a signal processing device 3, and an ultrasonic waveform display device 4 such as an oscilloscope.

The signal processing device 3 performs, for example, the calculation of the attenuation rate of the ultrasonic multiple echoes, the calculation of the amplification ratio between the incident ultrasonic echo and the reflection ultrasonic echo, and the signal processing for improving the SN ratio of a multiple reflection echo signal. Note that the pipe to be inspected has a pipe main body 5 made of iron or stainless steel. The inner surface of the pipe main body 5 is provided with a plastic or rubber lining 6. A fluid (couplant) 10 suppresses the reflection of the ultrasonic wave on the surface of the pipe main body 5.

In such a structure, an ultrasonic echo 7 is introduced into the pipe main body 5 through the outer surface thereof to detect an ultrasonic echo 8 from the lining 6 and the inner surface of the pipe main body 5. Thus, the separation between the pipe main body 5 and the lining 6 can be detected.

Figure 9:
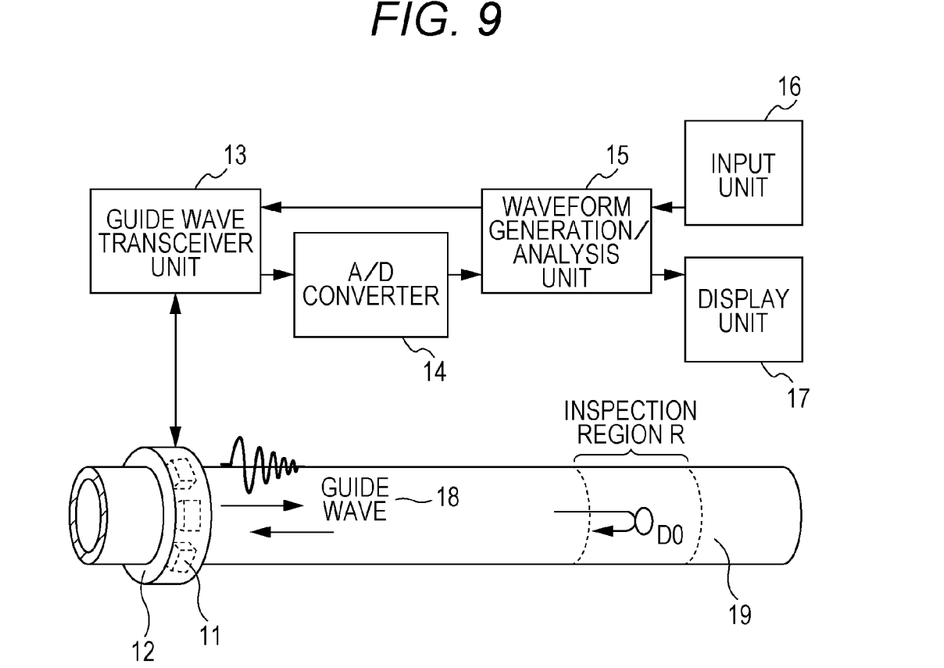
FIG. 9 is an explanatory diagram illustrating an example of an apparatus that detects the corrosion or erosion in a pipe by using a guide wave.

FIG. 9 is a diagram illustrating an exemplary structure of an apparatus for detecting the corrosion and erosion of the pipe by using a guide wave (JP-A-2005-10055). As illustrated in FIG. 9, a guide wave transceiver 11 is a device that generates a guide wave 18 in a pipe 19 and includes, for example, a piezoelectric element. The guide wave transceiver 11 is disposed in contact with the pipe 19, and is electrically connected to a guide wave transceiver unit 13 through a coaxial cable.

A transceiver ring 12 is a jig for annularly holding a plurality of guide wave transceivers 11 around the pipe. The transceiver ring 12 preferably includes a structure configured to house the guide wave transceivers 11 at equal intervals in a circumferential direction and a structure detachable from the pipe. The transceiver ring 12 has a ring-shaped frame with a structure that can be divided into two. In other words, the ring-shaped frame can be assembled by cutting a ring-shaped component into two divided pieces along the diameter of the ring and connecting the ends of the respective divided pieces together using a screw. Thus, as the divided pieces are connected together to surround the outer periphery of the pipe 19, the transceiver ring 12 can be attached around the outer periphery of the pipe 19.

On the inside of the ring-shaped frame of the transceiver ring 12, the plurality of guide wave transceivers 11 are housed. Moreover, the inside of the ring-shaped frame is supported by a spring that extends or contracts relative to the outer peripheral surface of the pipe 19. Therefore, upon the attachment of the transceiver ring 12 to the outer peripheral surface of the pipe 19, the spring presses the plurality of guide wave transceivers 11 are against the outer peripheral surface of the pipe 19. Thus, the guide wave transceivers 11 can easily generate the guide wave 18 to the pipe 19.

The guide wave transceiver unit 13 applies a transmission waveform to the guide wave transceiver 11 to transmit the guide wave 18. Moreover, the guide wave transceiver unit 13 amplifies the reception waveform from the guide wave transceiver 11. The guide wave transceiver unit 13 is connected to a waveform generation/analysis unit 15 to enable the communication of digital data. The guide wave transceiver unit 13 is connected to an A/D converter 14 through the coaxial cable for transmitting a reception waveform to the A/D converter 14.

The A/D converter 14 has a function to convert an analogue signal into a digital signal. The A/D converter 14 is connected to the guide wave transceiver unit 13 and the waveform generation/analysis unit 15. Thus, the A/D converter 14 is able to convert the reception waveform of the guide wave 18 output from the guide wave transceiver unit 13 into the digital waveform to communicate with the waveform generation/analysis unit 15.

The waveform generation/analysis unit 15 generates the transmission waveform and analyzes the reception waveform, while controlling the entire operation of a pipe inspection apparatus. The waveform generation/analysis unit 15 includes a computer or the like. The waveform generation/analysis unit 15 is connected to an input unit 16 such as a keyboard that accepts the instruction from a user, and to a display unit 17 such as a CRT.

In such a structure, the thickness, the material, and the sound velocity of the pipe, a region R to be inspected, and the reference waveform are input to the waveform generation/analysis unit 15. The waveform of the reception wave (reception waveform) when the guide wave according to the reference waveform is reflected on a defect Do at the center of the region R to be inspected and is received at the guide wave transceiver 11 is calculated based on the thickness and the material. Transmission waveforms are generated so that the calculated reception waveforms can be transmitted in order from the late reception time.

The guide wave transceiver unit 13 applies a signal based on the transmission waveform to the guide wave transceiver 11 to generate the guide wave 18. The guide wave transceiver unit 13 receives the reception waveform of the guide wave 18 from the guide wave transceiver 11. The A/D converter 14 converts the signal into a digital signal. The waveform generation/analysis unit 15 displays the digital signal on the display unit 17 as an inspection result.

The pipe corrosion can be roughly divided into two types. One is called general corrosion, in which the inside of the pipe is uniformly corroded due to the flowing fluid and the wall of a pipe (hereinafter, also referred to as a pipe wall) is reduced in thickness uniformly. This corrosion often appears in a carbon steel pipe or the like. For the general corrosion, for example, an ultrasonic thickness meter is set at any point on the tube. The appropriate countermeasure can be taken by recognizing the thickness measured with the ultrasonic thickness meter as the thickness of the entire pipe wall.

The other type of the pipe corrosion is called localized corrosion in which the thickness reduction (pitting) or damage progresses locally. The corrosion often appears in a stainless steel pipe or the like. The localized corrosion can be detected when the corrosion has occurred in the place where the ultrasonic thickness meter is set. However, it is impossible to detect the localized corrosion that has occurred in a generation place different from the place where the ultrasonic thickness meter is set.

SUMMARY

An ultrasonic pipe measurement apparatus includes: a plurality of ultrasonic transceivers discretely disposed on a pipe wall of a pipe; and a control unit configured to control the plurality of ultrasonic transceivers and detect a generation point of damage caused in the pipe based on an ultrasonic signal exchanged between the ultrasonic transceivers.

DETAILED DESCRIPTION

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The major problem of localized corrosion in a pipe is that the generation point thereof cannot be predicted. In view of this, the pipe may be covered with ultrasonic thickness meters. This method, however, is not practical from the economical point of view. Here, the use of a guide wave enables the detection of a damage due to localized corrosion at a relatively far point in the pipe. However, for propagating the guide wave, the wall thickness of the pipe serves as a limiting factor. Moreover, it is difficult to measure the size of corrosion, for example, the diameter of a pitting, which is one kind of localized corrosion. In the case where the size of the localized corrosion cannot be detected, it is difficult to take an appropriate countermeasure.

One of the objects of the present disclosure is to provide an ultrasonic pipe measurement apparatus that can detect localized corrosion and scale attached to the inside of the pipe, measure the generation point and the size or amount of each of them, and take an appropriate countermeasure as necessary without covering the pipe with the ultrasonic transceivers.

An ultrasonic pipe measurement apparatus according to an embodiment of the present disclosure includes: a plurality of ultrasonic transceivers discretely disposed on a pipe wall of a pipe; and a control unit configured to control the plurality of ultrasonic transceivers and detect a generation point of damage caused in the pipe based on an ultrasonic signal exchanged between the ultrasonic transceivers.

The number of ultrasonic transceivers may be three or more.

The control unit may be configured to detect a generation point of the damage caused in the pipe based on time after the ultrasonic wave is output from one ultrasonic transceiver and before a reflection wave from the damage is received by each ultrasonic transceiver.

The control unit may be configured to measure a size of the damage caused in the pipe based on the ultrasonic signal exchanged between the ultrasonic transceivers.

The control unit may be configured to measure the size of the damage caused in the pipe based on an amplitude of the reflection wave from the damage received by the ultrasonic transceiver.

The control unit may have operation modes including a search mode wherein an interval of transmitting an ultrasonic pulse is set relatively long, the search mode being, the search mode being adapted to detect a point of the damage and the approximate size of the damage, and a measurement mode adapted to accurately measure the size of the damage, the measurement mode allowing an ultrasonic pulse with an amplitude and a transmission interval sufficient for required accuracy to be transmitted; and the control unit may be configured to maintain the operation mode to be the search mode when the size of the damage measured in the search mode is less than or equal to a predetermined threshold.

The control unit may be configured to switch the operation mode from the search mode to the measurement mode when the size of the damage measured in the search mode is greater than the predetermined threshold.

The control unit may be configured to switch the operation mode from the measurement mode to the search mode when the size of the damage measured in the measurement mode is less than or equal to the predetermined threshold.

The control unit may be configured to execute both the search mode and the measurement mode when a plurality of damages with different sizes is detected.

The control unit may be configured to sequentially switch the ultrasonic transceivers that transmit the ultrasonic waves.

The plurality of ultrasonic transceivers may be configured to transmit the ultrasonic waves with different frequencies.

This enables the following without covering the pipe with the ultrasonic transceivers: the detection of localized corrosion and scale attached to the inside of the pipe; the measurement of the generation point and the size or amount of each of them; and an appropriate countermeasure when needed.

Figure 1:
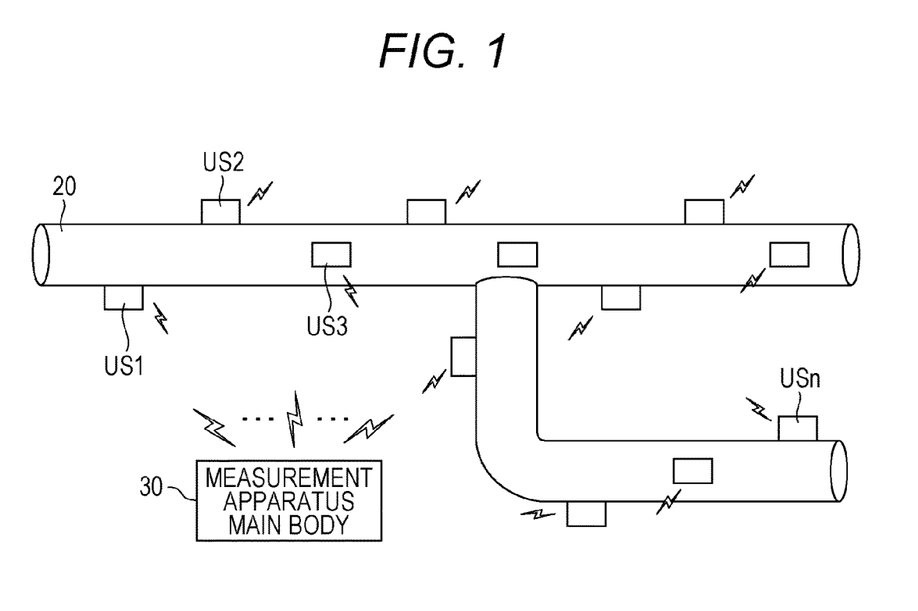
FIG. 1 is a block diagram illustrating an embodiment of the present disclosure.

An embodiment of the present disclosure is described below with reference to the drawings. FIG. 1 is a block diagram illustrating an embodiment of the present disclosure. As illustrated in FIG. 1, a plurality of ultrasonic transceivers US1 to USn is attached to an outer wall of a pipe 20 discretely in the direction of the pipe 20. The number of ultrasonic transceivers US1 to USn may be three or more. In the description below, for example, the outer diameter of the pipe 20 is set to approximately 100 mm, the distance between the adjacent ultrasonic transceivers is set to approximately 1000 mm, and the frequency of the ultrasonic wave is set to approximately 50 kHz to 5 MHz.

The ultrasonic transceivers US1 to USn are connected to a measurement apparatus main body (control unit) 30 in a wired or wireless manner, and transmit and receive ultrasonic signals to and from the pipe 20 according to the control from the measurement apparatus main body 30. Note that the ultrasonic transceivers US1 to USn are disposed evenly throughout the pipe 20 in some cases while the ultrasonic transceivers US1 to USn are concentrated on important points in other cases. The ultrasonic transceivers US1 to USn are not operated individually. Two or more of them can be operated in cooperation.

The measurement apparatus main body 30 has functions of generation, calculation, and the like with respect to an ultrasonic signal transmitted and output to the ultrasonic transceivers US1 to US2. The calculation function is a function of subjecting reception signals from at least three of the ultrasonic transceiver US1 to USn to arithmetic processing to determine the point, outer diameter, depth (thickness of pipe wall), and the like of the damage of the pipe 20 caused by the corrosion or erosion.

Figure 2:
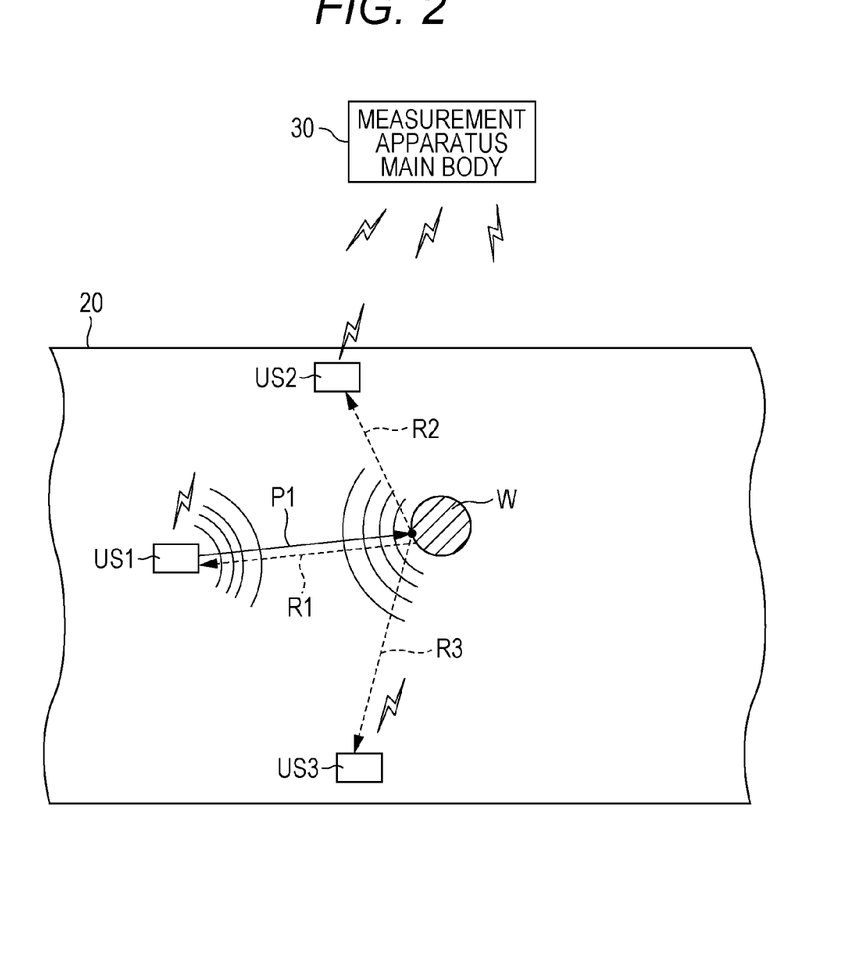
FIG. 2 is an explanatory diagram of the operation for detecting the point of damage in a pipe caused by corrosion or erosion.

FIG. 2 is a diagram illustrating the operation for detecting the point of damage W of the pipe 20 caused by the corrosion or erosion. As illustrated in FIG. 2, first, an ultrasonic pulse is output from the ultrasonic transceiver US1. The output ultrasonic pulse (ultrasonic signal) propagates along the pipe wall of the pipe 20 and reaches the damage W caused by the corrosion or erosion.

Part of the ultrasonic signal (transmission wave P1) is reflected on this damage W and part of the reflection wave (reflection wave R1) returns to the ultrasonic transceiver US1. Parts of the reflection wave, reflection waves R2 and R3, are received by other ultrasonic transceivers US2 and US3, respectively. The measurement apparatus main body 30 calculates the point of the damage W based on the propagation time T1 to T3 of the reflection waves R1 to R3 from the damage W by, for example, the triangulation method. Note that the reflection wave is not generated when the damage is not present in the measurement region. The propagation time T1 to T3 of the reflection waves R1 to R3 refers to the time required from when the ultrasonic pulse is output (transmitted) from the ultrasonic transceiver US1 to when the reflection waves R1 to R3 from the damage W are received by the ultrasonic transceivers US1 to US3.

Figure 3A:
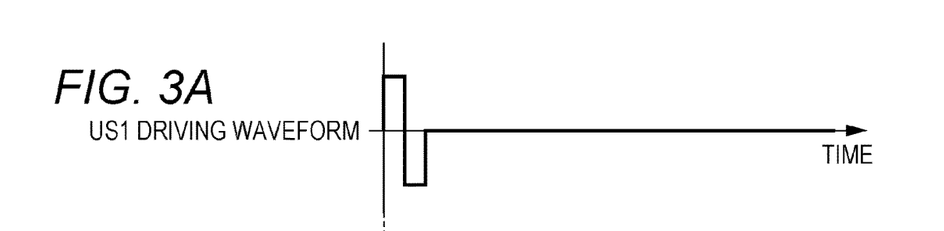
FIGS. 3A to 3D are diagrams illustrating examples of the waveforms in each portion in the structure of FIG. 2.
Figure 3B:
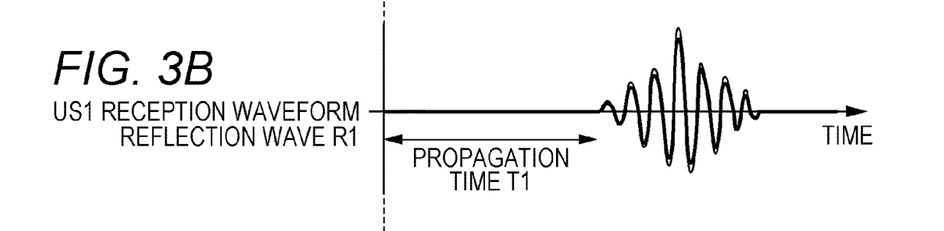
Figure 3C:
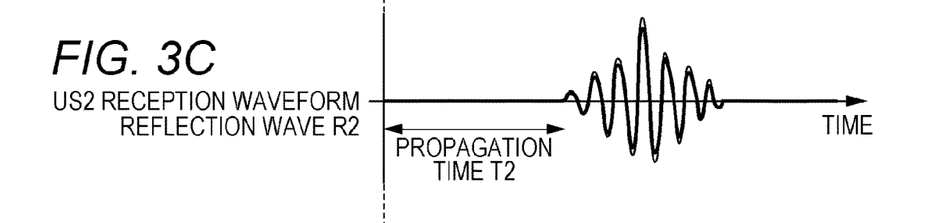
Figure 3D:
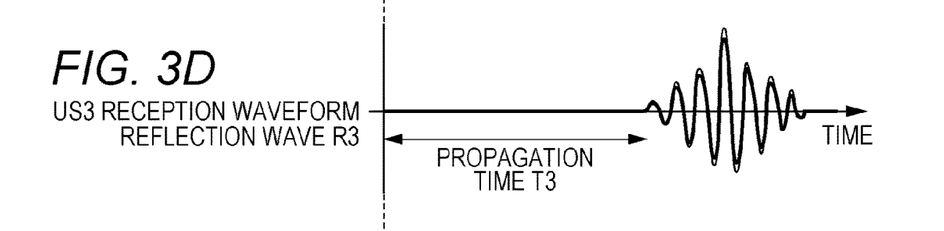

FIGS. 3A to 3C are diagrams illustrating examples of the waveforms in each portion in the structure of FIG. 2. FIG. 3A illustrates the driving waveform of the ultrasonic transceiver US1. FIG. 3B illustrates the waveform of the reflection wave R1 received by the ultrasonic transceiver US1. FIG. 3C illustrates the reception waveform of the reflection wave R2 received by the ultrasonic transceiver US2. FIG. 3D illustrates the reception waveform of the reflection wave R3 received by the ultrasonic transceiver US3.

The operation mode with a main purpose of detecting the point of the damage W caused by the corrosion or the erosion is referred to as a search mode. In this search mode, the corrosion velocity predicted from the nature and flow rate of the fluid and the material of the pipe is taken into consideration. For example, the intervals of transmitting the ultrasonic pulses (transmission intervals, the output intervals) are set relatively long from the viewpoint of lower energy consumption (for example, once a day or once in several days or weeks). The measurement apparatus main body 30 identifies the point of the damage at the transmission intervals. Then, the measurement apparatus main body 30 obtains the rough values of the outer diameter and depth of the detected damage. In other words, the search mode is the operation mode wherein the interval of transmitting the ultrasonic is set relatively long, the search mode being adapted to detect the point of the damage and the approximate size of the damage.

Figure 4:
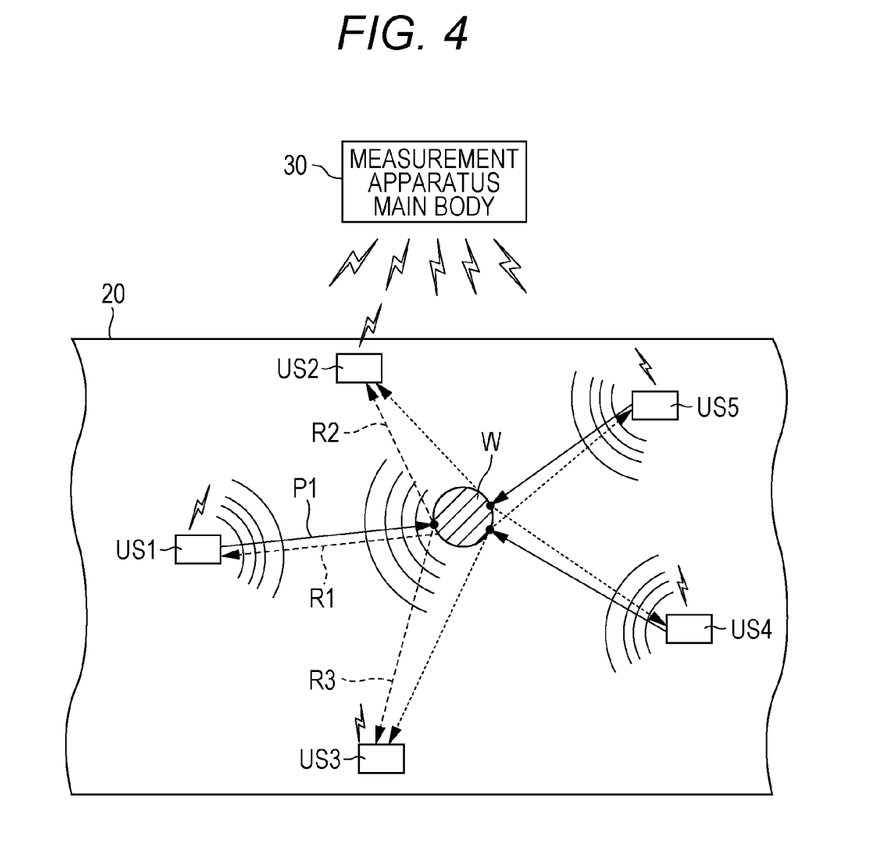
FIG. 4 is an explanatory diagram of the operation for measuring the outer diameter of damage in a pipe caused by corrosion or erosion.

FIG. 4 is a diagram illustrating the operation for measuring the outer diameter of the damage W of the pipe 20 caused by the corrosion or erosion. For measuring the outer diameter of the damage W, the measurement apparatus main body 30 measures the end face around the damage by using the ultrasonic signals output from the ultrasonic transceivers including US2 and US3, which are the transceivers other than the transceiver US1.

Figure 5:
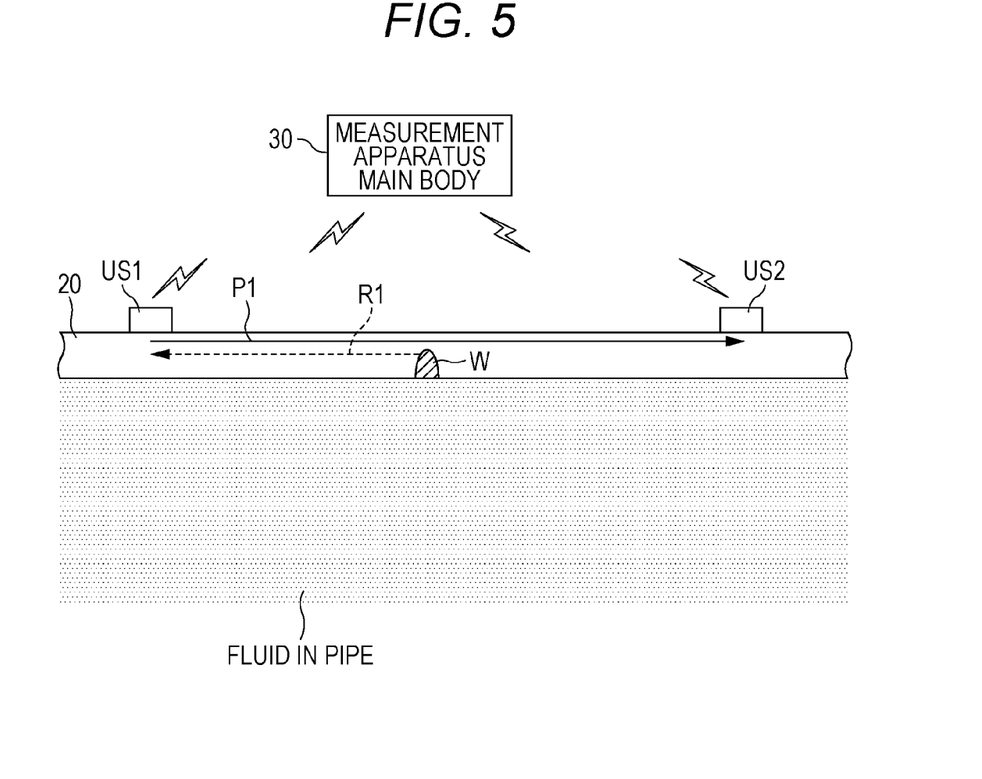
FIG. 5 is an explanatory diagram of the operation for measuring the depth of damage in a pipe caused by corrosion or erosion.
Figure 6A:
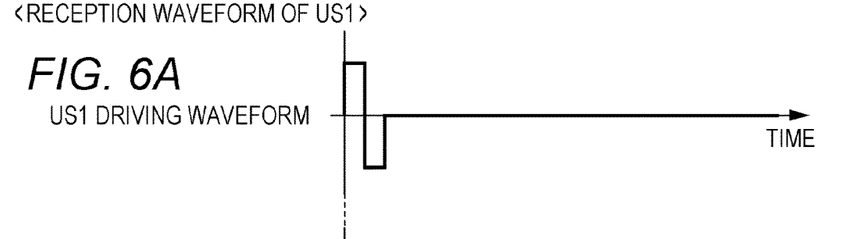
FIGS. 6A to 6F are diagrams illustrating examples of the waveforms in each portion in the structure of FIG. 5.
Figure 6B:
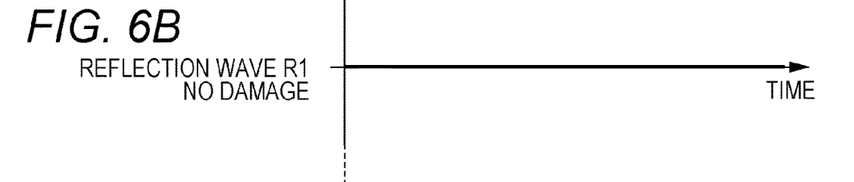
Figure 6C:
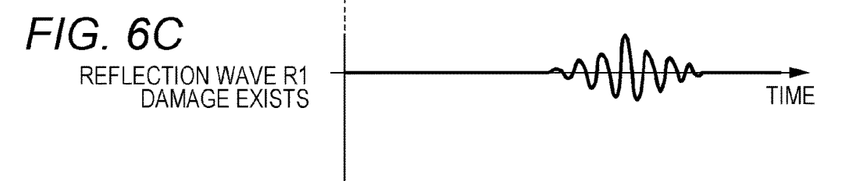
Figure 6D:
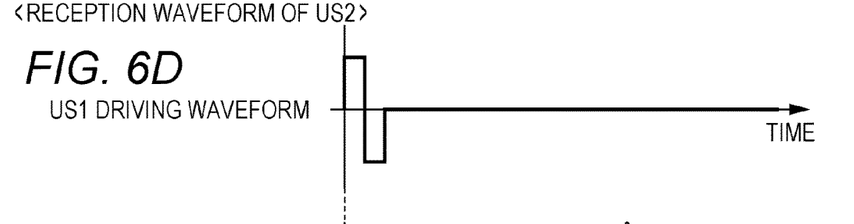
Figure 6E:
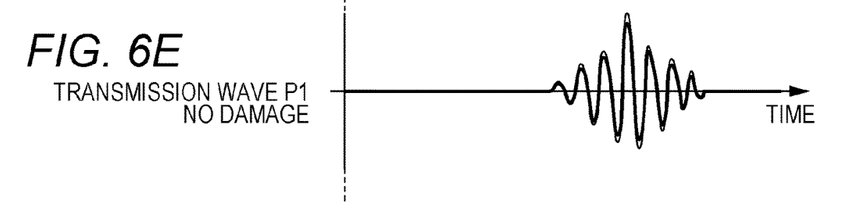
Figure 6F:
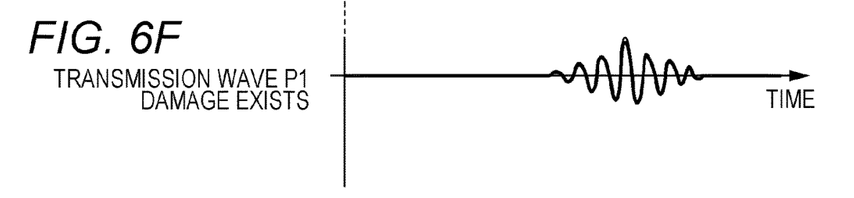

FIG. 5 is a diagram illustrating the operation for measuring the depth of the damage W of the pipe 20 caused by the corrosion or erosion. FIGS. 6A to 6F are diagrams illustrating examples of the waveforms in each portion in the structure of FIG. 5. FIG. 6A and FIG. 6D illustrate the driving waveform of the ultrasonic transceiver US1. FIG. 6B and FIG. 6C illustrate the reception waveform of the ultrasonic transceiver US1. FIG. 6E and FIG. 6F illustrate the reception waveform of the ultrasonic transceiver US2. First, attention is paid to the reception waveform of the ultrasonic transceiver US1. In the absence of the damage W, the reflection wave R from the damage W is not generated. Therefore, the amplitude of the reception waveform in the ultrasonic transceiver US1 does not appear as illustrated in FIG. 6B. In the presence of the damage W, the reflection wave R1 is generated. Therefore, the amplitude of the reception waveform in the ultrasonic transceiver US1 appears as illustrated in FIG. 6C. The magnitude of the amplitude depends on the depth of the damage W. In other words, the measurement apparatus main body 30 can measure the size of the damage W in the pipe 20 based on the amplitudes of the reflection waves from the damage W that are received by the ultrasonic transceivers US1 to USn.

Next, attention is paid to the reception waveform of the ultrasonic transceiver US2. In the absence of the damage W, the ultrasonic transceiver US2 substantially directly receives the transmission wave P1 of the ultrasonic transceiver US1 as illustrated in FIG. 6E. Thus, the amplitude of the reception waveform of the ultrasonic transceiver US2 becomes sufficiently large. In the presence of the damage W, the amplitude of the reception waveform of the ultrasonic transceiver US2 is reduced depending on the depth of the damage W as illustrated in FIG. 6F.

Accordingly, the measurement apparatus main body 30 can measure the depth of the damage W based on the magnitude of the amplitude of the reception waveform in the ultrasonic transceiver US1 and/or US2. Specifically, when the size of the damage W detected in the search mode is less than or equal to a predetermined threshold, the measurement apparatus main body 30 sets the operation mode to the search mode (maintains the search mode). On the other hand, when the size of the damage W detected in the search mode is greater than the predetermined threshold, the measurement apparatus main body 30 transits the operation mode from the search mode to the measurement mode. In the measurement mode, the measurement apparatus main body 30 controls the plurality of ultrasonic transceivers provided around the damage W so as to transmit the ultrasonic pulses with the amplitudes and transmission intervals enough for the required accuracy. In other words, the measurement mode is the operation mode adapted to accurately measure the size of the damage, in which the ultrasonic pulses with the amplitudes and transmission intervals enough for the required accuracy are transmitted.

In the measurement mode, the measurement apparatus main body 30 accurately measures the size of the damage W that is greater than the predetermined threshold. Moreover, the measurement apparatus main body 30 accurately measures the change in size of the damage W over time, i.e., the progressing velocity of the damage W. For increasing the accuracy, the ultrasonic transceivers US1 to USn apply the pulse signals with higher energy in this measurement mode than in the search mode.

As a method of increasing the energy of the signal, the amplitude may be increased and the number of pulses may be increased to form burst waves, for example. The measurement method is basically the same as the method in the search mode.

By shortening the intervals of measurement as necessary, the fast-progressing damage W can be dealt with. By accurately measuring the size and progressing velocity of the damage W, these can be used as the indicator for the next action of a user. The next action corresponds to, for example, the exchange of pipes and the injection of an anticorrosive.

The outer diameter of the damage W measured roughly in the search mode is measured with high accuracy in the measurement mode. As a result, in fact, the diameter of the damage W may be less than or equal to the threshold. In this case, the measurement apparatus main body 30 may set the operation mode back to the search mode from the measurement mode. In other words, in this case, the measurement apparatus main body 30 may switch the operation mode from the measurement mode to the search mode.

The above embodiment has described the case of driving the ultrasonic transceiver US1 (the case in which the ultrasonic transceiver US1 transmits the ultrasonic signal). In fact, however, the other ultrasonic transceivers US2 to USn may carry out the operation similar to the ultrasonic transceiver US1 in the order of US2→US3→ . . . . In this case, the measurement apparatus main body 30 switches the ultrasonic transceivers US1 to USn in order and operates the transceivers as the transmitters. For distinguishing the ultrasonic signals transmitted from the ultrasonic transceivers US1 to USn, the measurement apparatus main body 30 causes the ultrasonic transceivers US1 to USn to transmit the ultrasonic signals in order while deviating the transmission timing. The amount of time deviation is set to, for example, the amount enough to avoid the interference. The measurement apparatus main body 30 manages the amount of time deviation.

As another method of distinguishing the ultrasonic signals transmitted from the ultrasonic transceivers US1 to USn, the frequency of the pulse transmitted may be changed for every one of the ultrasonic transceivers US1 to USn. In other words, the ultrasonic transceivers US1 to USn may be configured to transmit the ultrasonic pulses with different frequencies. In this case, the reception side (measurement apparatus main body 30) distinguishes between the ultrasonic signals from the ultrasonic transceivers US1 to USn (transmitters) through a band pass filter or the like. The measurement apparatus main body 30 also manages the selection of the transmission frequency and the band pass filter. According to this method, the plurality of ultrasonic transceivers can transmit the ultrasonic signals at the same time.

Description is made of the coexistence of the search mode and the measurement mode. For example, some damages in the measurement target region of the pipe 20 have a size of greater than a threshold while others have a size of less than or equal to the threshold. In this case, the measurement apparatus main body 30 may execute both the search mode and the measurement mode when it has been determined that a plurality of damages with different sizes exists in the search mode or the measurement mode (when the plurality of damages with different sizes have been detected). In other words, the measurement apparatus main body 30 may operate the ultrasonic transceivers US1 to USn in the measurement mode relative to the damage with the size greater than the threshold. The measurement apparatus main body 30 may operate the ultrasonic transceivers US1 to USn in the search mode relative to the other damages. Thus, the search mode and the measurement mode coexist in the entire ultrasonic pipe measurement apparatus.

Even in the occurrence of another damage in the pipe 20 during the operation in the measurement mode, the damage can be detected by the coexistence of the search mode and the measurement mode. As a method of the coexistence, for example, there are a method of repeating the search mode and the measurement mode by time division and a method of identifying the point of the damage while the measurement mode is maintained. In this case, the measurement apparatus main body 30 is set so that, for example, the detection of the damage and the measurement of the point of the damage are possible even in the measurement mode.

Figure 7:
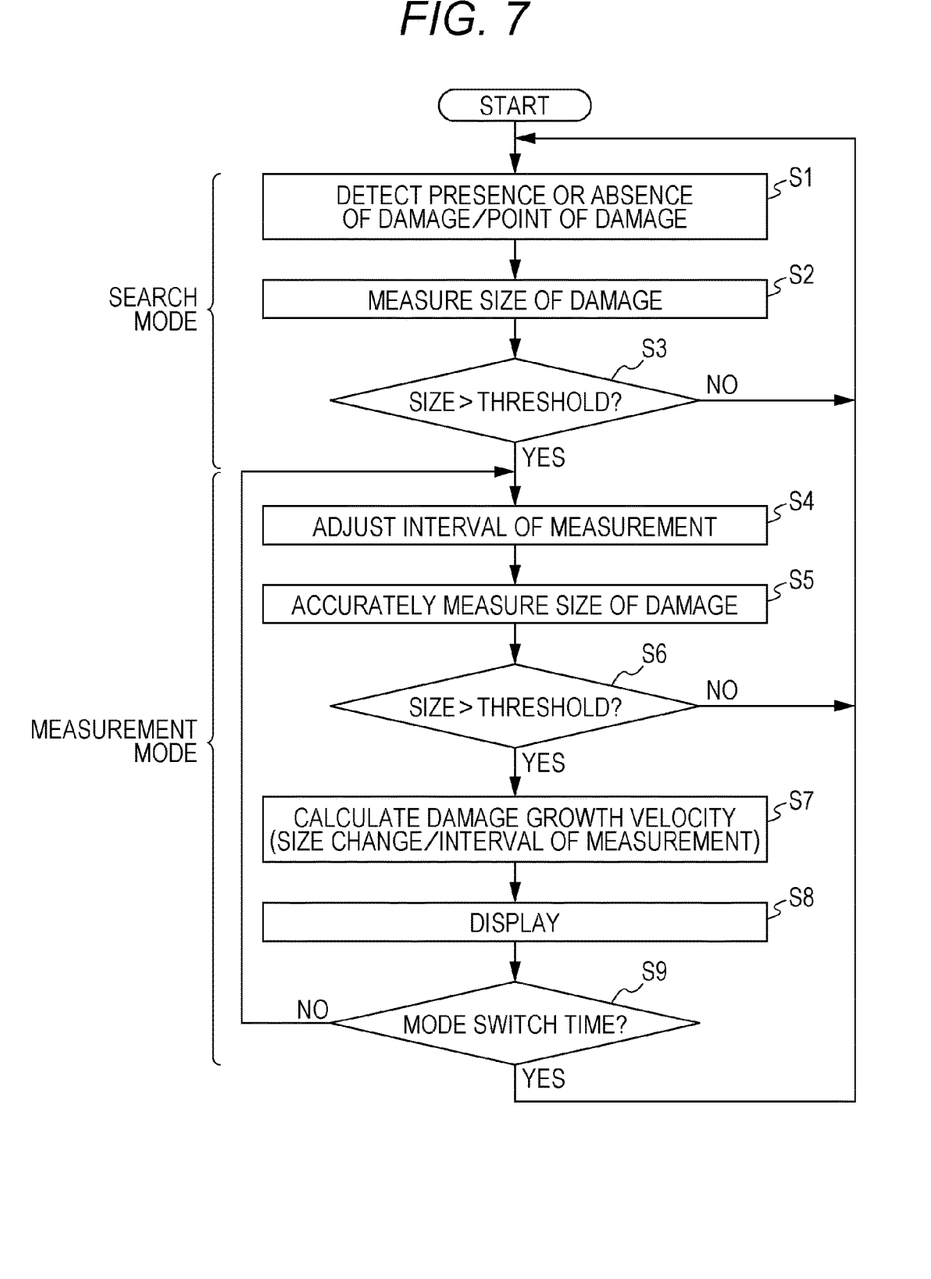
FIG. 7 is a flowchart of the operation of the entire apparatus.

FIG. 7 is a flowchart of the operation of the apparatus. First, the measurement apparatus main body 30 detects the presence or absence of, and the point of the damage caused by the corrosion or erosion in the pipe 20 (Step S1). Subsequently, the measurement apparatus main body 30 measures the size of the damage (Step S2). The measurement apparatus main body 30 determines whether the measured size of the damage is greater than a predetermined threshold (Step S3). The aforementioned operation steps are in the search mode.

When the measured size of the damage is greater than the predetermined threshold, the measurement apparatus main body 30 transits the operation mode from the search mode to the measurement mode. The measurement apparatus main body 30 adjusts the measurement time intervals (Step S4) and measures the size of the damage with high accuracy (Step S5). The measurement apparatus main body 30 determines whether the accurate measurement result on the size of the damage is greater than a predetermined threshold (Step S6).

When the accurate measurement result on the size of the damage is greater than the predetermined threshold, the measurement apparatus main body 30 calculates the damage growth velocity (Step S7) by dividing the change in size of the damage by the measurement time intervals, and displays the calculation result (Step S8). Note that the measurement apparatus main body 30 repeats the process from Step S4 to Step S8 in the measurement mode while adjusting the measurement time intervals as appropriate.

When the measurement result on the size of the damage is not greater than the threshold in Step S3 and Step S6 and the time has reached the mode switch time in Step S9, the measurement apparatus main body 30 returns to Step S1 and repeats the process from the search mode to the measurement mode.

In the above embodiment, as an example, attention is paid to the propagation time of the ultrasonic wave and the amplitude of the signal in the detection of the damage caused by the corrosion or erosion in the pipe. However, the signal parameter used in the detection of the damage is not limited to the propagation time and the amplitude. The measurement apparatus main body 30 can obtain various pieces of information by focusing on other signal parameters (using other signal parameters).

The measurement apparatus main body 30 may use, for example, the frequency spectrum. By the nonlinear phenomenon generated when the ultrasonic wave is reflected on the damage, the high-order harmonic wave and/or the ½ harmonic wave may be produced. The reflection wave from the opposite surface of the pipe wall propagates the most efficiently when the pipe wall thickness is the integral multiple of the half wavelength by a resonance phenomenon. Thus, the frequency spectrum of the reception wave includes the clear peak at the frequency according to the pipe wall thickness. Therefore, by observing the frequency spectrum of the reception signal, the measurement apparatus main body 30 can measure the state of the damage in the pipe and the pipe wall thickness (detect the general corrosion and detect the localized corrosion such as pitting right under the ultrasonic transceivers US1 to USn).

Further, the measurement apparatus main body 30 can measure the size of the damage more accurately by using the phase shift amount when the frequency spectrum is used.

Alternatively, the measurement apparatus main body 30 may use the cepstrum used in the audio signal processing, etc. Through the cepstrum analysis of the signal distortion due to the damage, the measurement apparatus main body 30 can extract the distortion of the signal, i.e., the feature data of the damage (such as the size). Thus, the measurement apparatus main body 30 can perform various signal processes on the signals from the plurality of ultrasonic transceivers US1 to USn disposed in the pipe. This enables the measurement apparatus main body 30 to detect the generation point of the damage and measure the size of the damage.

The above embodiment has described the ultrasonic transceivers US1 to USn as a single device. By the use of a phased array, the directions where the ultrasonic waves are transmitted from the ultrasonic transceivers US1 to USn can be controlled arbitrarily.

In each embodiment, the measurement apparatus main body 30 may drive the ultrasonic transceivers US1 to USn at the same time by applying the phase difference to the ultrasonic waves transmitted from the ultrasonic transceivers US1 to USn. This enables the ultrasonic transceivers US1 to USn to operate similar to the phased array as a whole.

In the above embodiment, as an example, the measurement apparatus main body 30 detects the generation point of the damage caused by the corrosion or erosion in the pipe and measures the size of the damage. The measurement apparatus main body 30 can similarly detect and measure the scale attached to the inner wall of the pipe.

As described above, according to the embodiment of the present disclosure, the ultrasonic pipe measurement apparatus that can achieve the following can be provided: the measurement of the state of the pipe including the generation point and the size of the damage in the pipe caused by the corrosion or erosion and the scale attached to the inside of the pipe without covering the pipe with the ultrasonic transceivers; and the necessary appropriate countermeasure.

The measurement apparatus main body 30 may set the operation mode to the measurement mode when the detected size of the damage W is greater than a predetermined threshold and set the operation mode to the search mode when the detected size of the damage W is less than or equal to the predetermined threshold.

According to the ultrasonic pipe measurement apparatus of this embodiment, the localized corrosion can be detected without covering the pipe with the ultrasonic transceivers, whereby the generation point and the size of the corrosion and the scale attached to the inside of the pipe can be measured and the appropriate countermeasure can be taken as necessary.

In the search mode, in view of the rate of progress of the corrosion that is predicted from the nature and flow rate of the fluid, the pipe material, and the like, for example, from the viewpoint of lower energy consumption, the interval of transmitting the ultrasonic pulses is set relatively long, for example, once a day or once in several days or weeks to identify the generation point of the damage. Then, in regard to the detected outer diameter and depth of the damage, the rough values may be measured.

In regard to FIGS. 6A to 6F, attention is paid to the reception waveform of the ultrasonic transceiver US1. When the damage W does not exist, the reflection wave R1 is not generated; thus, the amplitude of the reception waveform is not observed as illustrated in FIG. 6B. On the other hand, when the damage W exists, the reflection wave R1 is generated as illustrated in FIG. 6C and the magnitude of the amplitude depends on the depth of the damage W. Meanwhile, attention is paid to the reception waveform of the ultrasonic transceiver US2. When the damage W does not exist, the amplitude is large because the transmission wave P1 of the ultrasonic transceiver US1 is received substantially directly as illustrated in FIG. 6B. When the damage W exists, the amplitude of the reception waveform is attenuated depending on the depth of the damage W as illustrated in FIG. 6C.

The operation similar to that of the ultrasonic transceiver US1 may be applied to the ultrasonic transceivers in the order of US2→US3→ . . . so that the ultrasonic transceivers operate as the transmitter. For example, the ultrasonic transceivers may transmit the signals in order while deviating the timing in order to distinguish the ultrasonic signals transmitted from the ultrasonic transceivers. The amount of time deviation may be set to the amount enough to avoid the interference. In the case where there are a plurality of damages in the measurement target region of the pipe 20 and some damages have a size of greater than a threshold and other damages have a size of less than or equal to the threshold, the entire ultrasonic pipe measurement apparatus may allow the coexistence of the search mode and the measurement mode by conducting the measurement mode for the damages with the size greater than the threshold and the search mode for the other damages. Even in the occurrence of another damage in the pipe 20 during the operation in the measurement mode, the damage can be detected by the coexistence of the search mode and the measurement mode. As a method of the coexistence, for example, there are a method of repeating the search mode and the measurement mode by time division and a method of identifying the point of the damage while the measurement mode is maintained. In other words, the detection of the damage and the measurement of the point may be enabled in the measurement mode. In the above embodiment, the direction where the ultrasonic wave is transmitted may be controlled arbitrarily by the use of the phased array. By driving the ultrasonic transceivers in the above embodiment at the same time while applying the phase difference thereto, the entire transceivers can operate in a manner similar to the phased array.

The ultrasonic pipe measurement apparatus according to the embodiment may be any of the following first to fourth ultrasonic pipe measurement apparatus.

A first ultrasonic pipe measurement apparatus is an ultrasonic pipe measurement apparatus that measures a state of a pipe by using an ultrasonic wave, wherein: at least three ultrasonic transceivers are provided discretely on a pipe wall of the pipe; and the generation point of damage caused in the pipe and the size thereof are measured based on an ultrasonic signal exchanged between the ultrasonic transceivers.

A second ultrasonic pipe measurement apparatus is the first ultrasonic pipe measurement apparatus wherein: the operation mode includes a search mode and a measurement mode; the search mode is employed when the size of the damage is less than a predetermined threshold; the measurement mode is employed when the size of the damage is greater than the predetermined threshold; and the two modes coexist when a plurality of damages with different sizes exists.

A third ultrasonic pipe measurement apparatus is the second ultrasonic pipe measurement apparatus wherein: the operation mode is switched from the search mode to the measurement mode when the size of the damage from low-accurate measurement in the search mode has exceeded the predetermined threshold.

A fourth ultrasonic pipe measurement apparatus is the second or third ultrasonic pipe measurement apparatus wherein: in the search mode, the point of the damage is detected while suppressing the output by setting the interval of transmitting ultrasonic pulses relatively long; and in the measurement mode, the ultrasonic pulses with an amplitude and transmission interval sufficient for required accuracy is transmitted.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. An ultrasonic pipe measurement apparatus comprising:
a plurality of ultrasonic transceivers comprising at least a first transceiver, a second transceiver and a third transceiver, each discretely disposed on a pipe wall of a pipe at different positions along an axial length of the pipe; and
a control unit configured to (a) control the plurality of ultrasonic transceivers and (b) detect a generation point of damage caused in the pipe based on an ultrasonic signal transmitted by the first transceiver and received by at least said first, second and third ultrasonic transceivers, wherein
the control unit is configured to measure a size of the damage caused in the pipe based on the ultrasonic signal transmitted by the first transceiver and received by each of said at least first, second and third ultrasonic transceivers,
the control unit has operation modes including:
a search mode wherein an interval of transmitting ultrasonic pulses is set relatively long relative to a measurement mode, the search mode being adapted to detect a point of the damage and the approximate size of the damage; and
the measurement mode adapted to accurately measure the size of the damage, the measurement mode allowing an ultrasonic pulse with an amplitude and a transmission interval for required accuracy to be transmitted, and
the control unit is configured to maintain the operation mode to be the search mode when the size of the damage measured in the search mode is less than or equal to a predetermined threshold.

2. The ultrasonic pipe measurement apparatus according to claim 1, wherein the control unit is configured to detect a generation point of the damage caused in the pipe based on time after the ultrasonic wave is output from said first ultrasonic transceiver and before a reflection wave from the damage is received by each of said at least first, second and third ultrasonic transceiver.

3. The ultrasonic pipe measurement apparatus according to claim 1, wherein the control unit is configured to measure the size of the damage caused in the pipe based on an amplitude of the reflection wave from the damage as received by each of said at least first, second and third ultrasonic transceivers.

4. The ultrasonic pipe measurement apparatus according to claim 1, wherein the control unit is configured to switch the operation mode from the search mode to the measurement mode when the size of the damage measured in the search mode is greater than the predetermined threshold.

5. The ultrasonic pipe measurement apparatus according to claim 1, wherein the control unit is configured to switch the operation mode from the measurement mode to the search mode when the size of the damage measured in the measurement mode is less than or equal to the predetermined threshold.

6. The ultrasonic pipe measurement apparatus according to claim 1, wherein the control unit is configured to execute both the search mode and the measurement mode when a plurality of damages with different sizes is detected.

7. The ultrasonic pipe measurement apparatus according to claim 1, wherein the control unit is configured to sequentially switch the ultrasonic transceivers that become the first transceiver and transmit the ultrasonic waves.

8. The ultrasonic pipe measurement apparatus according to claim 1, wherein the plurality of ultrasonic transceivers are configured to transmit the ultrasonic waves with different frequencies.

* * * * *